(12) United States Patent
White, Jr. et al.

(10) Patent No.: US 6,740,311 B2
(45) Date of Patent: May 25, 2004

(54) ORAL COMPOSITIONS

(75) Inventors: Donald James White, Jr., Fairfield, OH (US); Kathleen Marie Kozak, Fairfield, OH (US); Vincent Bercovici, Isleworth (GB); Robert Francis Date, Woking (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/178,275

(22) Filed: Jun. 24, 2002

(65) Prior Publication Data

US 2003/0039617 A1 Feb. 27, 2003

Related U.S. Application Data

(60) Provisional application No. 60/300,766, filed on Jun. 25, 2001.

(51) Int. Cl.⁷ ............................. A61K 7/16; A61K 7/20
(52) U.S. Cl. ............................................. 424/49; 424/724
(58) Field of Search ............................. 424/49–58, 724

(56) References Cited

U.S. PATENT DOCUMENTS

| | | | |
|---|---|---|---|
| 3,574,823 A | 4/1971 | Roberts et al. | |
| 4,340,583 A | 7/1982 | Wason | |
| 4,420,312 A | 12/1983 | Wason | |
| 4,421,527 A | 12/1983 | Wason | |
| 4,631,184 A | 12/1986 | Winyall et al. | |
| 4,753,791 A | 6/1988 | Muller et al. | |
| 5,035,879 A | 7/1991 | Aldcroft et al. | |
| 5,108,734 A | 4/1992 | Colodney et al. | |
| 5,279,815 A | 1/1994 | Wason et al. | |
| 5,589,160 A * | 12/1996 | Rice | 424/49 |
| 5,603,920 A * | 2/1997 | Rice | 424/49 |
| 5,651,958 A * | 7/1997 | Rice | 424/49 |
| 5,658,553 A * | 8/1997 | Rice | 424/49 |
| 5,676,932 A * | 10/1997 | Wason et al. | 424/49 |
| 5,698,327 A | 12/1997 | Persello | |
| 5,716,601 A * | 2/1998 | Rice | 424/52 |
| 5,869,028 A * | 2/1999 | McGill et al. | 424/49 |
| 5,891,421 A * | 4/1999 | McGill et al. | 424/49 |
| 5,939,051 A | 8/1999 | Santalucia et al. | |
| 5,964,937 A | 10/1999 | Stanier | |
| 6,074,629 A | 6/2000 | Kostinko et al. | |
| 6,290,933 B1 | 9/2001 | Durga et al. | |
| 6,294,155 B1 | 9/2001 | Thomas et al. | |
| 6,342,205 B1 | 1/2002 | Niemi et al. | |
| 6,379,654 B1 | 4/2002 | Gebreselassie et al. | |
| 6,403,059 B1 * | 6/2002 | Martin et al. | 423/335 |
| 6,419,174 B1 * | 7/2002 | McGill et al. | 423/335 |

FOREIGN PATENT DOCUMENTS

| | | |
|---|---|---|
| EP | 0 535 943 A1 | 4/1993 |
| WO | WO 92/02454 A1 | 2/1992 |

* cited by examiner

*Primary Examiner*—Frederick F Krass
(74) *Attorney, Agent, or Firm*—Emelyn deLeon Hiland

(57) ABSTRACT

Oral care compositions comprising unique silica abrasives and methods for polishing and cleaning dental enamel using these oral care compositions are disclosed.

7 Claims, No Drawings

ORAL COMPOSITIONS

CROSS REFERENCE

This application claims priority under Title 35, United States Code 119(e) from Provisional Application Serial No. 60/300,766 filed Jun. 25, 2001.

TECHNICAL FIELD

The present invention relates to dentifrice compositions such as toothpastes comprised of single or mixed abrasive systems including specialized silica abrasives, and methods for cleaning and polishing dental enamel using these silica dentifrice compositions.

BACKGROUND OF THE INVENTION

An effective dentifrice composition should include the maintenance and preservation of tooth appearance through the removal of dental stains and the polishing of the teeth. It should clean and remove exogenous debris as well, thereby aiding the prevention of tooth decay and promoting gingival health. Abrasives aid in the removal of the tightly adherent pellicle film to which dental stains are affixed. Pellicle film usually comprises a thin acellular, glycoprotein-mucoprotein coating, which adheres to the enamel within minutes after teeth are cleaned. The presence of various food pigments lodged within the film accounts for most instances of teeth discoloration. Ideally, an abrasive should provide satisfactory cleaning by removal of the pellicle film with minimal abrasive damage to oral tissue, i.e. the dentin and enamel. In addition to cleaning action, it is desirable for abrasive systems to provide polishing of tooth surfaces, as polished surfaces may be more resistant to ectopic deposition of undesirable components. Importantly, tooth appearance may be improved by imparting a polished character to the teeth, as the surface roughness, e.g., polish, affects light reflectance and scattering, which are integrally related to how teeth visibly appear. The surface roughness also affects tooth feel; i.e, polished teeth have a clean, smooth and slick feel.

The use of a variety of agents to clean the oral cavity and reduce plaque and mouth malodor has been recognized for some time. Examples include: U.S. Pat. No. 3,696,191, Oct. 3, 1972 to Weeks; U.S. Pat. No. 3,991,177, Nov. 9, 1976 to Vidra et al.; U.S. Pat. No. 4,058,595, Nov. 15, 1977 to Colodney; U.S. Pat. No. 4,115,546, to Vidra et al.; U.S. Pat. No. 4,138,476, Feb. 6, 1979 to Simonson et al.; U.S. Pat. No. 4,140,758, Feb. 20, 1979 to Vidra et al.; U.S. Pat. No. 4,154,815, May 15, 1979 to Pader; U.S. Pat. No. 4,737,359, Apr. 12, 1988 to Eigen et al.; U.S. Pat. No. 4,986,981, Jan. 22, 1991 to Glace et al.; U.S. Pat. No. 4,992,420, Feb. 12, 1991 to Nesser; U.S. Pat. No. 5,000,939, Mar. 19, 1991 to Dring et al.; JP Kokai 02/105,898, published Apr. 18, 1990 to Kao Corporation; JP Kokai 03/128,313, published May 31, 1991 to Nippon Kotai Kenkyu and JP Kokai 03/223,209, published Oct. 2, 1991 to Lion Corporation; U.S. Pat. No. 4,652,444, Mar. 24, 1987 to Maurer; U.S. Pat. No. 4,725,428, Feb. 16, 1988 to Miyahara et al.; U.S. Pat. No. 4,355,022, Oct. 19, 1982 to Rabussay and PCT application WO 86/02831, published May 22, 1986 to Zetachron, Inc.

Abrasives are described in U.S. Pat. No. 4,340,583, Jul. 20, 1982 to Wason, U.S. Pat. No. 3,574,823, Apr. 13, 1971 to Roberts et al., EP Patent 535,943A1, Apr. 7, 1993, McKeown et al., and PCT Application WO 92/02454, Feb. 20, 1992 to McKeown et al., U.S. Pat. No. 5,603,920, issued Feb. 18, 1997 and U.S. Pat. No. 5,716,601, issued Feb. 10, 1998 both to Rice describe oral compositions, such as oral gels and toothpastes containing a low structure precipitated silica having a narrow particle size range distribution of soft particles and a mean value (MV) particle size ranging from 8 to 14 microns, providing unique cleaning efficacy contrasted against hard tissue abrasivity effects.

Even with the many disclosures relating to compositions for pellicle cleaning and antiplaque activity, the need for improved products still exists. The present inventors have discovered that the benefits of precipitated silica compositions extend beyond cleaning with controlled and acceptable abrasivity. Indeed, specialized silica abrasives have been discovered that can be formulated in oral care compositions to provide unique polishing benefits to tooth enamel surfaces, in addition to cleaning and stain removal. The polishing benefits include improved teeth appearance as well as positive tooth feel characteristics.

The present invention therefore relates to oral care products and methods of using the same to provide pellicle cleaning using precipitated silica abrasives, which impart improved enamel polishing without undue increases in hard tissue abrasivity. The present compositions and methods also provide benefits in effectively arresting the accumulation of plaque and preventing gum disease. Still further, the present invention provides compositions and methods that will also abate subsequent calculus formation.

SUMMARY OF THE INVENTION

The present invention relates to dentifrice compositions comprising:

a. an orally-acceptable carrier and b. a silica abrasive comprising a precipitated silica having a mean value (MV) particle size distribution ranging from 8 to 14 microns and a 10% Brass Einlehner Abrasion (10% BEA) value of greater than about 7, wherein the precipitated silica abrasive, when formulated into a dentifrice, provides effective pellicle cleaning as measured by a Pellicle Cleaning Ratio (PCR) of about 70 to 140, acceptable levels of abrasivity of below a Radioactive Dentin Abrasion value (RDA) of 250, and improvements in tooth surface polishing beyond that achieved with conventional precipitated silicas.

The present silica abrasives may be used alone or in combination with other abrasives preferably relatively softer silica abrasives having 10% BEA values below about 7. The present silica abrasive compositions provide at least about a 20% improvement in tooth surface polishing as measured in an Enamel Polishing Index Model developed in our laboratories. The present invention further relates to a method of cleaning and polishing teeth, reducing plaque, gingivitis and calculus using the above compositions.

These and other features, aspects, and advantages of the present invention will become evident to those skilled in the art from the following detailed description.

DETAILED DESCRIPTION OF THE INVENTION

While the specification concludes with claims, which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

All percentages and ratios herein are by weight unless otherwise specified. Polishing Index, PCR and RDA are unitless. Additionally, all measurements are made at 25° C., unless otherwise specified.

Herein, "comprising" means that other steps and other ingredients which do not affect the end result can be added. This term encompasses the terms "consisting of" and "consisting essentially of".

The oral composition of the present invention may be in the form of a toothpaste, dentifrice, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side.

The term "dispenser", as used herein, means any pump, tube, or container suitable for dispensing toothpaste.

The oral composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition may be a single phase oral composition or may be a combination of two or more oral compositions.

The term "orally-acceptable carrier" as used herein means a suitable vehicle, which can be used to apply the present compositions to the oral cavity in a safe and effective manner. Such vehicle may include materials such as fluoride ion sources, additional anticalculus agents, buffers, other abrasive materials, peroxide sources, alkali metal bicarbonate salts, thickening materials, humectants, water, surfactants, titanium dioxide, flavor system, sweetening agents, xylitol, coloring agents, and mixtures thereof.

By "safe and effective amount" as used herein, means a sufficient amount to clean teeth and reduce stain/plaque/gingivitis/calculus without harming the tissues and structures of the oral cavity.

The pH of the present herein described compositions ranges from about 4.5 to about 9.5, with the preferred pH being from about 6.5 to about 9.0 and the most preferred pH being 7.0 to about 9.0.

The essential as well as optional components of the compositions of the present invention are described in the following paragraphs.

Silica Abrasive

The precipitated silicas of the present invention provide unique enamel polishing activity values. These silicas are especially characterized by having a 10% Brass Einlehner Abrasion values ranging from greater than about 7, preferably from about 10 to about 19 and having a mean value (MV) particle size in the range of about 8 to about 14 as measured on a Microtrac Particle Analyzer. The MV particle size takes into account skewed particle sizes and speaks to distribution of the particle sizes of individual or average aggregates of particles. Thus, as the mean particle size increases over the range of about 8 to about 14 microns as disclosed herein, it would be expected that the Radioactive Enamel Abrasion and Radioactive Dentin Abrasion (REA and RDA) values would also increase. While RDA and REA might also increase with hardness, it has been heretofore unappreciated that differences in silica particle hardness, within the range of particle size about 8 to about 14 microns, could produce increases in enamel polishing within acceptable RDA values. These silicas also have good fluoride compatibility, and in particular compatibility with sodium fluoride and stannous fluoride sources.

The precipitated silicas of the invention are low structure silicas in accordance with the definitions set forth in the *J. Soc. Cosmet. Chem.* 29., 497–521 (August, 1978), and *Pigment Handbook*: Volume 1, Properties and Economics, 2nd Edition, Edited by Peter A. Lewis, John Wiley & Sons, Inc., 1988, p. 139–159.

The Pellicle Cleaning Ratio (PCR) of the precipitated silica of the invention, which is a measure of the cleaning characteristics of a dentifrice, ranges from about 70 to about 140 and preferably from about 105 to about 125.

The Radioactive Dentin Abrasion (RDA) of the inventive silicas, which is a measure of the abrasiveness of the precipitated silicas of the invention when incorporated into a dentifrice is less than about 250, preferably ranging from about 100 to about 225, more preferably from about 150 to about 200.

The present precipitated silicas have an oil absorption ranging from about 50 to 65 cc/100 g, oil absorption and pH as measured in a 5% aqueous slurry of from about 7 to about 8. Further, the present precipitated silicas may be characterized in terms of their BET surface area, pour density, pack density, and porosity as determined by mercury intrusion (HGI) void volume measurements. These characteristics are comparable to those observed with prior art silicas such as disclosed in commonly-owned U.S. Pat. No. 5,603,920, issued Feb. 18, 1997 and U.S. Pat. No. 5,716,601, issued Feb. 10, 1998.

The present silicas, when incorporated into a dentifrice composition, provide an improved polishing effect on enamel surfaces. The improved polishing effect is heretofore unappreciated for silica dentifrices and within acceptable PCR/RDA ratios, defines a novel improvement in abrasive performance. The precipitated silicas of the invention are preferably characterized as synthetic hydrated amorphous silicas, also known as silicon dioxides or $SiO_2$. This definition is intended to include gels and hybrids of silicas such as Geltates.

Without wishing to be bound by theory, it is believed that this invention takes advantage of relatively harder silica abrasives that provide a unique polishing effect without the abrasiveness that would normally be expected from such harder silicas.

The RDA (Radioactive Dentin Abrasion) values are determined according to the method set forth by Hefferren, *Journal of Dental Research*, July–August 1976, pp. 563–573, and described in Wason, U.S. Pat. Nos. 4,340,583, 4,420,312 and 4,421,527. The PCR (Pellicle Cleaning Ratio) cleaning values are determined by a slightly modified version of the PCR test described in "In Vitro Removal of Stain With Dentifrice", G. K. Stookey, T. A. Burkhard and B. R. Schemerhorn, *J. Dental Research*, 61, 1236–9, 1982.

In the present specification, oil absorption is measured using the ASTM rub-out method D281. Surface area is determined by the BET nitrogen adsorption method of Brunaur et al., *J. Am. Chem. Soc.*, 60, 309 (1938). To measure brightness, fine powder materials that are pressed into a smooth surfaced pellet are evaluated using a Technidyne Brightimeter S-5/BC. This instrument has a dual beam optical system where the sample is illuminated at a angle of 45°, and the reflected light viewed at 0°. It conforms to TAPPI test methods T452 and T646, and ASTM Standard D985. A series of filters direct to reflected light of desired wavelengths to a photocell where it is converted to an output voltage. This signal is amplified and then processed by an internal microcomputer for display and printout.

The average particle size (mean value and median or 50%) is measured using a Microtrac II apparatus, Leeds and Northrup. Specifically, a laser beam is projected through a transparent cell which contains a stream of moving particles suspended in a liquid. Lights rays which strike the particles are scattered through angles which are inversely proportional to their sizes. The photodetector array measures the quantity of light at several predetermined angles. Electrical signals proportional to the measured light flux values are then processed by a microcomputer system to form a multichannel histogram of the particle size distribution.

The pore volumes (mercury pore volume) are determined using an Autopore II 9220 Porosimeter (Micromeritics Corporation). This instrument measures the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution. It identifies the most common pore size in the sample.

Bulk density is measured by measuring the volume in liters occupied by a given weight of the abrasive and is reported in pounds per cubic foot.

The silicas can be further characterized using an Einlehner At-1000 Abrader to measure the abrasiveness of the silicas in the following manner: In the Brass Einlehner Abrasion test, an Einlehner At-1000 Abrader is used as follows: (1) Fourdrinier brass wire screen is weighed and exposed to the action of a 10% aqueous silica suspension for a certain length of time; (2) the amount of abrasion is then determined as milligrams weight lost of the Fourdrinier wire screen per 100,000 revolutions. 10% Brass Einlehner (10% BEA) results are expressed in milligrams loss/100,100 revolutions.

The silicas preferably possess a 10% BEA value of greater than about 7, preferably greater than about 10 and preferably between about 15 and about 40.

The polishing effect of silicas is determined according to an enamel polishing index, a methodology developed in our laboratories. Bovine enamel surfaces expressing surface roughness values of between 0.55 and 0.7 Ra units are produced by abrasion with 300 grit silicon carbide sandpaper. Ra values are measured by a surface profilometer. These surfaces are brushed for 1600 strokes with slurries of test dentifrice comprised of one part dentifrice in 2.5 parts water with a medium bristled toothbrush at a normal surface force of 150 grams. The ratio of final surface roughness vs. initial roughness is multiplied by 100 and the improvements are expressed as % of initial values. The silicas in the present invention provide surface polishing effects superior to conventional silicas at comparable dosing or in admixture with known silica abrasives.

These precipitated silicas are prepared by a fresh water acidulation process wherein silica (silicon dioxide or $SiO_2$) is precipitated by reaction of an alkali metal silicate and a mineral acid in aqueous solution. The alkali metal silicate may be any alkali metal silicate, but sodium silicate is preferred. While any mineral acid may be used in the process, sulfuric acid is a preferred reactant.

It is a feature of the invention that the process of preparation is a fresh water process, that is, no electrolyte such as alum, $Na_2SO_4$, or NaCl, is present during the reaction.

In the preferred process, an aqueous sodium silicate solution is provided wherein the sodium silicate is present in a concentration of about 8.0 to 35 weight percent, preferably 8.0 to 15 weight percent. The $Na_2O:SiO_2$ ratio in the silicate solution should range from about 1 to 3.5:1 and preferably from 2.5 to 3.4:1. The sulfuric acid reactant will preferably have a concentration of about 6 to 35% in water, preferably about 9.0 to 15 weight percent.

In a preferred procedure, a small portion of the sodium silicate solution is charged to a reactor for reaction with the sulfuric acid and the remainder of the silicate. In a preferred embodiment, only about 1 to 5% of the total stoichiometric amount of sodium silicate solution, preferably about 2%, should be initially placed in the reactor to serve as initiating nuclei for the silica This aqueous solution of sodium silicate is then preheated to a temperature in the range of about 80 to 90° C. with agitation prior to the addition of the sulfuric acid and remainder of sodium silicate. Agitation may be provided by conventional stirring of agitation equipment. Thereafter with continued agitation, the remainder of the sodium silicate and sulfuric acid are separately slowly added to the reactor over a limited period of time. Preferably, the sodium silicate is metered into the reaction mixture at a rate of about 7 to 12 liters per minute and, more preferably, at the specific rate of 8.94 liters per minute. The sulfuric acid is metered into the reactor at the rate of about 1 to 4 liters per minute but more preferably at the rate of about 2.95 liters per minute.

The sodium silicate solution and sulfuric acid are metered into the sodium silicate solution in the reactor over an addition time of about 40 to 60 minutes, but preferably over a 50 minute addition time. At the end of this addition time at which point the silica has precipitated, the sodium silicate solution addition is stopped but sulfuric acid addition is continued with agitation until a final pH of 5.0 to 5.8 is obtained in the reactor. At this stage, the silica has precipitated to provide a mixture of the precipitated silica and the reaction liquor.

After precipitation of the silica and lowering of the pH of the mixture, the reaction mixture is then subjected to digestion and curing. Digestion is carried out by raising the temperature of the mixture to a temperature of 90° to 98° C., preferably about 95° to 98° C., with continued agitation, over a residence time of about 5 minutes to an hour preferably about 10 to 30 minutes.

Thereafter, the product is cured by further raising the temperature of the mixture to a temperature in the range of about 100° C. with continued agitation so as to boil the reaction mixture over a cure time of about one-half hour to about two hours, preferably about 30 minutes to 80 minutes, more preferably about 1 hour. Digestion and curing procedures are critical features of the invention.

On completion of the reaction, the pH is again adjusted to about 5.0, and reaction mixture is filtered and washed with water to remove salts from the filter cake. The filter cake is then dried, preferably by conventional spray drying to produce a precipitated silica containing about 3 to 10% moisture. If necessary, the precipitated silica may be milled to desired particle size by adjusting milling conditions. Because of the uniqueness of the process, milling conditions are easily adjusted to produce silica particles of desired mean values.

Preferred precipitated silica materials include those available from the J. M. Huber Corporation under the tradename, "Zeodent", particularly the silica carrying the designation "Zeodent 109" and "Zeodent 129". The present silica abrasives may be used alone or in combination with other abrasives preferably relatively softer silica abrasives having 10% BEA values below about 7, preferably ranging from about 3 to about 6. Examples of such softer silicas include those with the designation "Zeodent 118" and "Zeodent 119".

The total abrasive in the compositions described herein is present at a level of from about 6% to about 70%, preferably from about 15% to about 35% when the dentifrice is a toothpaste. Higher levels, as high as 95%, may be used if the composition is a toothpowder.

In addition to the above described essential components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, additional abrasives, and coloring agents. These and other optional components are further described in U.S. Pat. No. 5,004, 597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele.

ORALLY-ACCEPTABLE CARRIER

The carrier for the components of the present compositions can be any orally-acceptable vehicle suitable for use in the oral cavity. Such carriers include the usual components of toothpastes, tooth powders, prophylaxis pastes, lozenges, gums and the like and are more fully described hereinafter. Toothpastes are the preferred systems.

Surfactants

One of the preferred optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used or in combination with the sarcosinate surfactant in the compositions of the present invention. Suitable optional surfactants are described more fully in U.S. Pat. No. 3,959, 458, May 25, 1976 to Agricola et al.; U.S. Pat. No. 3,937, 807, Feb. 10, 1976 to Haefele; and U.S. Pat. No. 4,051,234, Sep. 27, 1988 to Gieske et al.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535, 421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethylammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Chelating Agents

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges, which help hold this biomass intact. However, it is not desired to use a chelating agent that has an affinity for calcium that is too high, as this may result in tooth demineralization, which is contrary to the objects and intentions of the present invention.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ to provide improved cleaning with reduced plaque and calculus formation.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7$-4 (e.g., ($HP_2O_7$-3)) may be present when a final product pH is established.

The pyrophosphate salts are described in more detail in Kirk & Othmer, *Encyclopedia of Chemical Technology*, Second Edition, Volume 15, Interscience Publishers (1968).

Optional agents to be used in place of or in combination with the pyrophosphate salt include such known materials as polyamino propane sulfonic acid (AMPS), zinc citrate trihydrate, polyphosphates (e.g., tripolyphosphate; hexametaphosphate), diphosphonates (e.g., EHDP; AHP), polyphosphonates, phosphonate copolymers, polypeptides (such as polyaspartic and polyglutamic acids), and mixtures thereof.

Examples of phosphonate copolymers are the diphosphonate-derivatized polymers in U.S. Pat. No. 5,011,913 to Benedict et al. A preferred polymer is diphosphonate modified polyacrylic acid. Suitable phosphonate-containing polymers such as shown below are described in U.S. Pat. No. 5,980,776 to Zakikhani, et al.

1. Co-polymer of acrylic acid and diphosphonic acid with structure:

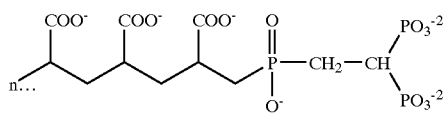

2. Co-polymer of acrylic acid and vinylphosphonic acid with structure:

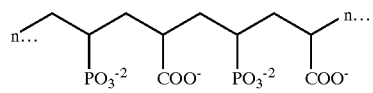

3. Co-polymer of methacrylic acid and vinlyphosphonic acid with structure:

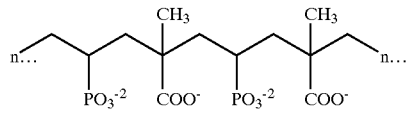

4. Co-polymer of acrylic acid and vinlydiphosphonic acid with structure:

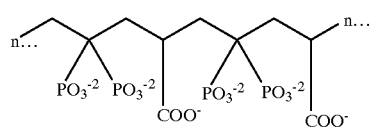

Polyphosphates are also optionally included in the present compositions. A polyphosphate is generally understood to consist of two or more phosphate molecules arranged primarily in a linear configuration, although some cyclic derivatives may be present. In addition to pyrophosphates and tripolyphosphate, which are technically polyphosphates, also desired are the polyphosphates having around four or more phosphate, i.e., tetrapolyphosphate and hexametaphosphate, among others. Polyphosphates larger than tetrapolyphosphate usually occur as amorphous glassy materials. Preferred in this invention are the linear "glassy" polyphosphates having the formula:

wherein X is sodium, potassium or ammonium and n averages from about 6 to about 125. Preferred are polyphosphates manufactured by FMC Corporation which are commercially known as Sodaphos (n≈6), Hexaphos (n≈13), and Glass H (n≈21). The most preferred polyphosphate is Glass H. These polyphosphates may be used alone or in a combination thereof.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether, poly-acrylic, polyitaconic and polymaleic acids, and sulfoacrylic oligomers of M.W. as low as 1,000 available as Uniroyal ND-2.

Fluoride Source

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include stannous fluoride, sodium fluoride, potassium fluoride, sodium monofluorophosphate and many others. Stannous fluoride and sodium fluoride are particularly preferred, as well as mixtures thereof.

Teeth Whitening Actives and Teeth Color Modifying Substances

Teeth whitening actives that may be used in the oral care compositions of the present invention include bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

Particles most useful in the present invention include pigments and colorants routinely used in the cosmetic arts. There are no specific limitations as to the pigment and, or colorant used in the present composition other than the limitation of the effect it has on the light source upon the teeth surfaces. Pigments and colorants include inorganic white pigments, inorganic colored pigments, pearling agents, filler powders and the like; see Japanese Published Patent Application Kokai No. 9-100215, published Apr. 15, 1997. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titanium dioxide, bismuth oxychloride, zinc oxide and mixtures thereof. Pigments that are generally recognized as safe, and are listed in C.T.F.A. Cosmetic Ingredient Handbook, 3rd Ed., Cosmetic and Fragrance Assn., Inc., Washington D.C. (1982).

The pigments are typically used as opacifiers and colorants. These pigments can be used as treated particles, or as the raw pigments themselves. Typical pigment levels are selected for the particular impact that is desired by the consumer. For example, for teeth that are particularly dark or stained one would typically use pigments in sufficient amount to lighten the teeth. On the other hand, where individual teeth or spots on the teeth are lighter than other teeth, pigments to darken the teeth may be useful. The levels of pigments and colorants are generally used in the range of about 0.05% to about 20%, preferably from about 0.10% to about 15% and most preferably from about 0.25% to about 10% of the composition.

Thickening Agents

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred Carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, issued Mar. 30, 1993 and U.S. Pat. No. 5,242,910, issued Sep. 7, 1993, both to Damani, and U.S. Pat. No. 4,443,430, to Mattei, issued Apr. 17, 1984.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant.

The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring and sweetening agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 10% to about 50%, and preferably from about 20% to about 40%, by weight of the aqueous toothpaste compositions herein. These amounts of water include the free water which is added plus that which is introduced with other materials, such as with sorbitol.

Titanium dioxide may also be added to the present composition. Titanium dioxide is a white powder, which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about 4.5 to about 9.5. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part toothpaste.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U. S. Pat. Nos. 4,849,213 and 4,528,180 to Schaeffer.

Suitable lozenge and chewing gum components are disclosed in U.S. Pat. No. 4,083,955, Apr. 11, 1978 to Grabenstetter et al.

Other Active Agents

The present oral compositions may also include other active agents, such as antimicrobial agents. Included among such agents are water insoluble non-cationic antimicrobial agents such as halogenated diphenyl ethers, phenolic compounds including phenol and its homologs, mono and polyalkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey. Other antimicrobials such as copper bisglycinate, copper glysinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranses, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to anti-microbial properties. Such agents are disclosed in U.S. Pat. No. 2,946,725, Jul. 26, 1960, to Norris et al. and in U.S. Pat. No. 4,051,234, Sep. 27, 1977 to Gieske et al. Other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from about 0.01% to about 5.0%, by weight of the dentifrice composition.

Method of Use

The present invention also relates to methods for cleaning and polishing teeth and reducing the incidence of stain, plaque, gingivitis and calculus on dental enamel.

The method of use herein comprises contacting a subject's dental enamel surfaces and oral mucosa with the oral compositions according to the present invention. The method of treatment may be by brushing with a dentifrice or rinsing with a dentifrice slurry or mouthrinse. Other methods include contacting the topical oral gel, mouthspray, or other form with the subject's teeth and oral mucosa. The subject may be any person or lower animal whose tooth surface contact the oral composition.

It should be understood that the present invention relates not only to methods for delivering the present silica abrasive containing compositions to the oral cavity of a human, but also to methods of delivering these compositions to the oral cavity of other animals, e.g., household pets or other domestic animals, or animals kept in captivity.

For example, a method of use may include a person brushing a dog's teeth with one of the dentifrice composi-tions. Another example would include the rinsing of a cat's mouth with an oral composition for a sufficient amount of time to see a benefit. Pet care products such as chews and toys may be formulated to contain the present oral compositions. The composition including the silica abrasive agent is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Dentifrice compositions with different levels of silica abrasive(s) according to the present invention are shown in Examples I to IV below.

EXAMPLE I

| Component | Dentifrice A Weight % | Dentifrice B Weight % | Dentifrice C Weight % |
|---|---|---|---|
| Sorbitol Solution (70%) USP | 24.962 | 24.962 | 24.962 |
| Silica - Zeodent 109[1] | 30.000 | 15.000 | 10.000 |
| Silica - Zeodent 118[2] | — | 15.000 | — |
| Silica - Zeodent 119[3] | — | — | 10.000 |
| Thickening Silica | 1.000 | 1.000 | 1.000 |
| Water, Purified USP | 13.500 | 13.500 | 13.500 |
| Glycerin | 7.750 | 7.750 | 17.750 |
| Polyethylene Glycol 300, NF (PEG-6) | 6.000 | 6.000 | 6.000 |
| Tetrasodium Pyrophosphate, Anhydrous | 5.045 | 5.045 | 5.045 |
| Sodium Alkyl Solution (27.9%) | 5.000 | 5.000 | 5.000 |
| Sodium Bicarbonate | 1.500 | 1.500 | 1.500 |
| Poloxamer 407, NF | 1.250 | 1.250 | 1.250 |
| Flavor | 1.100 | 1.100 | 1.100 |
| Titanium Dioxide/Carnauba Wax Prills | 1.000 | 1.000 | 1.000 |
| Sodium Carboxymethyl Cellulose | 0.750 | 0.750 | 0.750 |
| Sodium Saccharin | 0.350 | 0.350 | 0.350 |
| Sodium Carbonate, Anhydrous | 0.500 | 0.500 | 0.500 |
| Sodium Fluoride | 0.243 | 0.243 | 0.243 |
| Color | 0.050 | 0.050 | 0.050 |
| Total | 100.000 | 100.000 | 100.000 |

[1]Zeodent 109 having 10% Brass Einlehner Abrasion values between 7 to 17.
[2]Zeodent 118 having 10% Brass Einlehner Abrasion values between 3.7 to 5.1.
[3]Zeodent 119 having 10% Brass Einlehner Abrasion values between 5 to 6.

EXAMPLE II

| Component | % Wt/Wt |
|---|---|
| Sorbitol (70%), low reducing sugars | 29.000 |
| Glycerin | 8.000 |
| PEG-6 | 6.000 |
| Hydrated silica, amorphous (Z119) | 11.500 |
| Hydrated silica, amorphous (Z109) | 11.500 |

EXAMPLE II-continued

| Component | % Wt/Wt |
| --- | --- |
| Carbomer 956 | 0.050 |
| Xanthan gum | 0.500 |
| Sodium alkyl sulfate, 28% | 7.000 |
| Sodium fluoride | 0.321 |
| Tetrapotassium pyrophosphate, 60% | 3.159 |
| Tetrasodium pyrophosphate | 1.908 |
| Disodium pyrophosphate | 1.344 |
| Triclosan | 0.280 |
| Titanium dioxide | 0.525 |
| Sodium saccharin | 0.300 |
| Flavor | 1.100 |
| Cellulose gum 7MF | 0.700 |
| Cetyl Dimethicone Copolyol | 1.000 |
| Water/minors | to 100 |

EXAMPLE III

| Component | % Wt/Wt |
| --- | --- |
| Sorbitol (70%), low reducing sugars | 29.000 |
| Glycerin | 8.000 |
| PEG-6 | 6.000 |
| Hydrated silica, amorphous (Z119) | 7.666 |
| Hydrated silica, amorphous (Z109) | 15.334 |
| Carbomer 956 | 0.050 |
| Xanthan gum | 0.500 |
| Sodium alkyl sulphate, 28% | 7.000 |
| Sodium fluoride | 0.321 |
| Tetrapotassium pyrophosphate, 60% | 3.159 |
| Tetrasodium pyrophosphate | 1.908 |
| Disodium pyrphosphate | 1.344 |
| Triclosan | 0.280 |
| Titanium dioxide | 0.525 |
| Sodium saccharin | 0.300 |
| Flavour | 1.100 |
| Cellulose gum 7MF | 0.700 |
| Cetyl Dimethicone Copolyol | 1.000 |
| Water/minors | to 100 |

EXAMPLE IV

| Component | % Wt/Wt |
| --- | --- |
| Sorbitol (70%), low reducing sugars | 29.000 |
| Glycerin | 8.000 |
| PEG-6 | 6.000 |
| Hydrated silica, amorphous (Z119) | 15.334 |
| Hydrated silica, amorphous (Z109) | 7.666 |
| Carbomer 956 | 0.050 |
| Xanthan gum | 0.500 |
| Sodium alkyl sulphate, 28% | 7.000 |
| Sodium fluoride | 0.321 |
| Tetrapotassium pyrophosphate, 60% | 3.159 |
| Tetrasodium pyrophosphate | 1.908 |
| Disodium pyrphosphate | 1.344 |
| Triclosan | 0.280 |
| Titanium dioxide | 0.525 |
| Sodium saccharin | 0.300 |
| Flavour | 1.100 |
| Cellulose gum 7MF | 0.700 |
| Cetyl Dimethicone Copolyol | 1.000 |
| Water/minors | to 100 |

The dentifrices from the Examples produce unanticipated improvements in enamel polishing characteristics, which improve overall benefits of tooth cleaning perception associated with these toothpastes. Table 1 highlights polishing improvements exhibited by precipitated silica abrasive Zeodent 109 having BEA values above 10, when used alone and in combination with softer silica abrasives including Zeodent 118 or Zeodent 119 wherein said polishing advantages are evident.

| Abrasive in Formulation | Polishing VS. BASELINE | Total Abrasive % Loading |
| --- | --- | --- |
| Z109, 30% | 43.10% | 30 |
| 15% Z118/15% Z109 | 42.32% | 30 |
| Z109, 20% | 36.13% | 20 |
| Z119, 30% | 35.63% | 30 |
| 10% Z118/10% Z109 | 29.49% | 20 |
| Z118, 30% | 25.54% | 30 |
| 10% 119/10% Z109 | 25.11% | 20 |
| Z118, 20% | 19.76% | 20 |
| Z119, 20% | 15.45% | 20 |
| Paste Supernate Liquid | 2.25% | 0 |

The effects of mixtures of abrasives are particularly noteworthy. Most specifically, it is shown that the addition of the Zeodent 109 silica as a 50% mixture with softer silicas produces polishing effects comparable to those achieved with the harder silica at doses comparable to the combined mixture dosage as illustrated herein. These improved polishing characteristics can be achieved with only partial substitution of the present unique silica with hardness values above BEA of 7, preferably above BEA of 10.

Importantly, the abrasive systems using the present silica with elevated abrasion and hardness characteristics by itself or in combination with prior art softer silicas result not only in increased enamel polishing but in increased pellicle cleaning ratio activity as well. A combination formula comprising 10% preferred Zeodent 109 abrasive with 10% Zeodent 119 abrasive produced PCR cleaning of 127 as compared with 83 produced by a formula containing 20% Zeodent 119 alone.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An abrasive dentifrice composition comprising:

(a) an orally-acceptable carrier and (b) a silica abrasive comprising a precipitated silica having a mean value (MV) particle size distribution ranging from about 8 to about 14 microns and a 10% Brass Einlehner Abrasion (10% BEA) value ranging from about 10 to about 19, wherein the precipitated silica abrasive, when formulated into a dentifrice, has a Pellicle Cleaning Ratio (PCR) of about 70 to 140, and a Radioactive Dentin Abrasion value (RDA) of about 100 to below about 250.

2. An abrasive dentifrice composition according to claim 1 comprising from about 6 to about 70% by weight of the composition of said precipitated silica abrasive.

3. An abrasive dentifrice composition comprising:

(a) an orally-acceptable carrier and (b) a mixed silica abrasive comprising
(i) a first precipitated silica having a mean value (MV) particle size distribution ranging from about 8 to about 14 microns and a 10% Brass Einlehner Abrasion (10% BEA) value ranging from about 10 to about 19, and (ii) a second precipitated silica having a 10% Brass Einlehner Abrasion (10% BEA) value of less than about 7, wherein the mixed precipitated silica abrasive, when formulated into a dentifrice, has a Pellicle Cleaning Ratio (PCR) of about 70 to 140, and a Radioactive Dentin Abrasion value (RDA) of about 100 to below about 250.

4. An abrasive dentifrice composition according to claim 3, wherein the second silica abrasive has a 10% Brass Einlehner Abrasion (10% BEA) value ranging from about 3 to about 6.

5. An abrasive dentifrice composition according to claim 3 comprising from about 6 to about 70% by weight of the composition of said mixed precipitated silica abrasive.

6. An abrasive dentifrice composition according to claim 3, wherein the mixed silica abrasive comprises 50% of the first silica abrasive and 50% of the second silica abrasive.

7. A method of cleaning and polishing teeth, and reducing plaque, gingivitis and calculus comprising applying an abrasive dentifrice composition according to claim 1 or claim 3, to the teeth of a user.

* * * * *